(12) United States Patent
Chen et al.

(10) Patent No.: US 9,388,166 B2
(45) Date of Patent: Jul. 12, 2016

(54) 6-AMINOINDOLE DERIVATIVES AS TRP CHANNEL ANTAGONISTS

(71) Applicant: Hoffmann-La Roche Inc., Little Falls, NJ (US)

(72) Inventors: Zhi Chen, Livingston, NJ (US); Shawn David Erickson, Leonia, NJ (US)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/689,828

(22) Filed: Apr. 17, 2015

(65) Prior Publication Data

US 2015/0218133 A1    Aug. 6, 2015

Related U.S. Application Data

(63) Continuation of application No. PCT/EP2013/071377, filed on Oct. 14, 2013.

(60) Provisional application No. 61/714,957, filed on Oct. 17, 2012.

(51) Int. Cl.
*C07D 401/14* (2006.01)
*C07D 401/04* (2006.01)
*C07D 209/12* (2006.01)

(52) U.S. Cl.
CPC ............ *C07D 401/14* (2013.01); *C07D 209/12* (2013.01); *C07D 401/04* (2013.01)

(58) Field of Classification Search
None
See application file for complete search history.

(56) References Cited

U.S. PATENT DOCUMENTS 8,871,759 B2 * 10/2014 Coburn ................ C07D 401/14
514/229.5

FOREIGN PATENT DOCUMENTS

| WO | 2007/091106 A2 | 8/2007 |
|---|---|---|
| WO | 2007/091106 A3 | 8/2007 |
| WO | 2009/019504 A1 | 2/2009 |

OTHER PUBLICATIONS

Dai et al., "Chemistry of aminophenols Part 2: A general and efficient synthesis of indoles possessing a nitrogen substituent at the C4, C5, C6, and C7 positions", TETRAHEDRON LETTERS (XP 002716058), 43:7699-7702 (2002).
Davies et al., "A highly active catalyst for the reduction cyclization of ortho-nitrostyrenes under mild conditions", TETRAHEDRON (XP 002716059), 61:6425-6437 (2005).
International Preliminary Report on Patentability issued in International Application No. PCT/EP2013/071377, dated Apr. 21, 2015, in 5 pages.
International Search Report issued in International Application No. PCT/EP2013/071377, dated Nov. 28, 2013, in 4 pages.
Sanz et al., "Straightforward selective preparation of nitro- or amino-indoles from 2-halonitroanilines and alkynes. First synthesis of 7-amino-5nitroindoles", TETRAHEDRON LETTERS (XP002716060), 50:4423-4426 (2009).

* cited by examiner

*Primary Examiner* — Timothy R Rozof
(74) *Attorney, Agent, or Firm* — Lily J. Ackerman

(57) ABSTRACT

The invention is concerned with the compounds of formula (I)

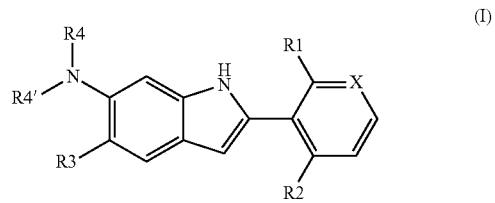

and pharmaceutically acceptable salts thereof. In addition, the present invention relates to methods of manufacturing and using the compounds of formula (I) as well as pharmaceutical compositions containing such compounds. The compounds of formula (I) can be used as medicament.

13 Claims, No Drawings

6-AMINOINDOLE DERIVATIVES AS TRP CHANNEL ANTAGONISTS

CROSS REFERENCE TO RELATED APPLICATIONS

This application is a continuation of International Application No. PCT/EP2013/071377 having an international filing date of Oct. 14, 2013, the entire contents of which are incorporated herein by reference, and which claims benefit under 35 U.S.C. §119 to U.S. Provisional Patent Application No. 61/714,957 filed Oct. 17, 2012, the entire contents of which are incorporated herein by reference.

The present invention relates to organic compounds useful for therapy and/or prophylaxis in a mammal of an inflammatory disease or disorder, and in particular to substituted indole compounds, their manufacture, pharmaceutical compositions containing them and their use as Transient Receptor Potential (TRP) channel antagonists.

The invention relates in particular to a compound of formula (I)

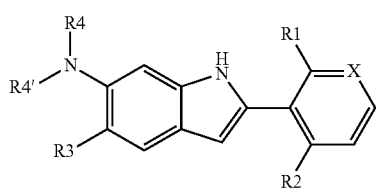

wherein:
X is —CH— or nitrogen;
R1 is lower alkoxy;
R2 is halogen;
R3 is hydrogen or lower alkoxy;
one of R4 and R4' is hydrogen or lower alkyl and the other is hydrogen or —C(O)—R5; and
R5 is alkoxy, —CF$_3$, —CHF$_2$, lower alkyl, chlorophenyl or (fluoro-benzenesulfonyl)-piperidinyl;
or a pharmaceutically acceptable salt thereof.

TRP channels are a class of ion channels found on the plasma membrane of a variety of human (and other animal) cell types. There are at least 28 known human TRP channels which are broken into a number of families or groups based upon sequence homology and function. TRPA1 is a non-selective cation conducting channel that modulates membrane potential via flux of sodium, potassium and calcium. TRPA1 has been shown to be highly expressed in the human dorsal root ganglion neurons and peripheral sensory nerves. In humans, TRPA1 is activated by a number of reactive compounds such as acrolein, allylisothiocyanate, ozone as well as unreactive compounds such as nicotine and menthol and is thus thought to act as a 'chemosensor'. Many of the known TRPA1 agonists are irritants that cause pain, irritation and neurogenic inflammation in humans and other animals. Therefore, it would be expected that TRPA1 antagonists or agents that block the biological effect of TRPA1 channel activators would be useful in the treatment of diseases such as asthma and its exacerbations, chronic cough and related maladies as well as being useful for the treatment of acute and chronic pain. Recently, it has also been shown that products of tissue damage and oxidative stress, e.g. 4-hydroxynonenal and related compounds, activate the TRPA1 channel. This finding provides additional rationale for the utility of small molecule TRPA1 antagonists in the treatment of diseases related to tissue damage, oxidative stress and bronchial smooth muscle contraction such as asthma, chronic obstructive pulmonary disease (COPD), occupational asthma, and virally-induced lung inflammation.

The invention also provides for pharmaceutical compositions comprising the compounds, methods of using the compounds and methods of preparing the compounds.

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables R1 to R6 of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g. trifluoromethyl, difluoromethyl, fluoromethyl, chloromethyl, etc.)

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl, in particular methyl.

The term "alkoxy" denotes a group of the formula —O—R', wherein R' is an alkyl group. The term "lower alkoxy," in turn, refers to an alkoxy moiety where the alkyl group R' has 1 to 7 carbon atoms. Examples of alkoxy moieties include methoxy, ethoxy, isopropoxy, and tert-butoxy, in particular methoxy and tert-butoxy.

The terms "halo", "halogen" and "halide", which may be used interchangeably, refer to a substituent fluoro, chloro, bromo or iodo, in particular chloro or iodo.

Unless otherwise indicated, the term "hydrogen" or "hydro" refers to the moiety of a hydrogen atom (—H) and not H$_2$.

The term "benzene", alone or in combination with other groups, means the phenyl moiety.

Unless otherwise indicated, the term "a compound of the formula" or "a compound of formula" or "compounds of the formula" or "compounds of formula" refers to any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula (I) (hydration).

Compounds that have the same molecular formula but differ in the nature or sequence of bonding of their atoms or the arrangement of their atoms in space are termed "isomers" and fall within the scope of the invention. Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses or, for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

The invention relates in particular to:

A compound of formula (I) wherein X is nitrogen;

A compound of formula (I) wherein X is —CH—;

A compound of formula (I) wherein R1 is methoxy;

A compound of formula (I) wherein R2 is iodine or chlorine;

A compound of formula (I) wherein R3 is hydrogen or methoxy;

A compound of formula (I) wherein R3 is hydrogen;

A compound of formula (I) wherein one of R4 and R4' is hydrogen or methyl and the other is hydrogen or —C(O)—R5;

A compound of formula (I) wherein R4 and R4' are both hydrogen;

A compound of formula (I) wherein R5 is methyl, tert-butoxy, —CF$_3$, —CHF$_2$, chlorophenyl or (fluoro-benzene-sulfonyl)-piperidinyl;

A compound of formula (I) wherein R5 is —CF$_3$; and

A compound of formula (I) selected from:
- [2-(4-Iodo-2-methoxy-pyridin-3-yl)-1H-indol-6-yl]-carbamic acid tert-butyl ester;
- 2,2,2-Trifluoro-N-[4-(4-iodo-2-methoxy-pyridin-3-yl)-1H-indol-6-yl]-acetamide;
- 2,2-Difluoro-N-[2-(4-iodo-2-methoxy-pyridin-3-yl)-1H-indol-6-yl]-acetamide;
- N-[2-(4-Chloro-2-methoxy-pyridin-3-yl)-1H-indol-6-yl]-2,2,2-trifluoro-acetamide;
- [2-(4-Iodo-2-methoxy-pyridin-3-yl)-1H-indol-6-yl]-methyl-amine;
- 2,2-Difluoro-N-[2-(4-iodo-2-methoxy-pyridin-3-yl)-1H-indol-6-yl]-N-methyl-acetamide;
- N-[2-(4-Iodo-2-methoxy-pyridin-3-yl)-1H-indol-6-yl]-N-methyl-acetamide;
- 2-(4-Iodo-2-methoxy-pyridin-3-yl)-5-methoxy-1H-indol-6-ylamine;
- 2-(2-Chloro-6-methoxy-phenyl)-1H-indol-6-ylamine;
- N-[2-(2-Chloro-6-methoxy-phenyl)-1H-indol-6-yl]-2,2,2-trifluoro-acetamide;
- 3-Chloro-N-[2-(4-iodo-2-methoxy-pyridin-3-yl)-1H-indol-6-yl]-benzamide;
- 3-Chloro-N-[2-(4-chloro-2-methoxy-pyridin-3-yl)-1H-indol-6-yl]-benzamide; and
- (S)-1-(4-Fluoro-benzenesulfonyl)-piperidine-2-carboxylic acid[2-(4-chloro-2-methoxy-pyridin-3-yl)-1H-indol-6-yl]-amide.

In the definition of R4 and R4', lower alkyl is advantageously methyl.

In the definition of R5, alkoxy is advantageously tert.-butoxy.

In another embodiment, the invention provides for a pharmaceutical composition, comprising a therapeutically effective amount of a compound according to formula (I) and a pharmaceutically acceptable carrier.

In another embodiment, the invention provides for a compound according to formula (I) for use as a therapeutically active substance.

In another embodiment, the invention provides for the use of a compound according to formula (I) for the treatment or prophylaxis of a respiratory disorder.

Examples of respiratory disorders are chronic obstructive pulmonary disorder (COPD), asthma, allergic rhinitis and bronchospasm.

In another embodiment, the invention provides for the use of a compound according to formula (I) for the preparation of a medicament for the treatment or prophylaxis of a respiratory disorder.

In another embodiment, the invention provides for a compound according to formula (I) for use in the treatment or prophylaxis of a respiratory disorder.

In another embodiment, the invention provides for a method for treating a respiratory disorder selected from chronic obstructive pulmonary disorder (COPD), asthma, allergic rhinitis and bronchospasm, comprising the step of administering a therapeutically effective amount of a compound according to formula (I) to a subject in need thereof.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis;* Wiley & Sons: New York, 1991, Volumes 1-15; *Rodd's Chemistry of Carbon Compounds,* Elsevier Science Publishers, 1989, Volumes 1-5 and Supplementals; and *Organic Reactions,* Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Compounds of the invention may be made by any number of conventional means. For example, they may be made according to the processes outlined in Scheme 1 below.

Unless indicated otherwise, R1-R4' and X have in the following schemes the meaning as defined above.

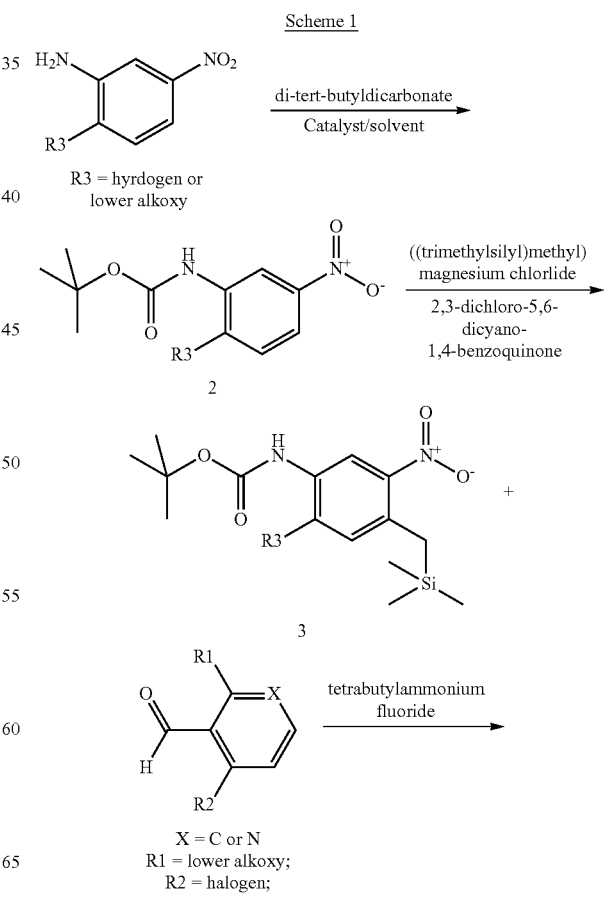

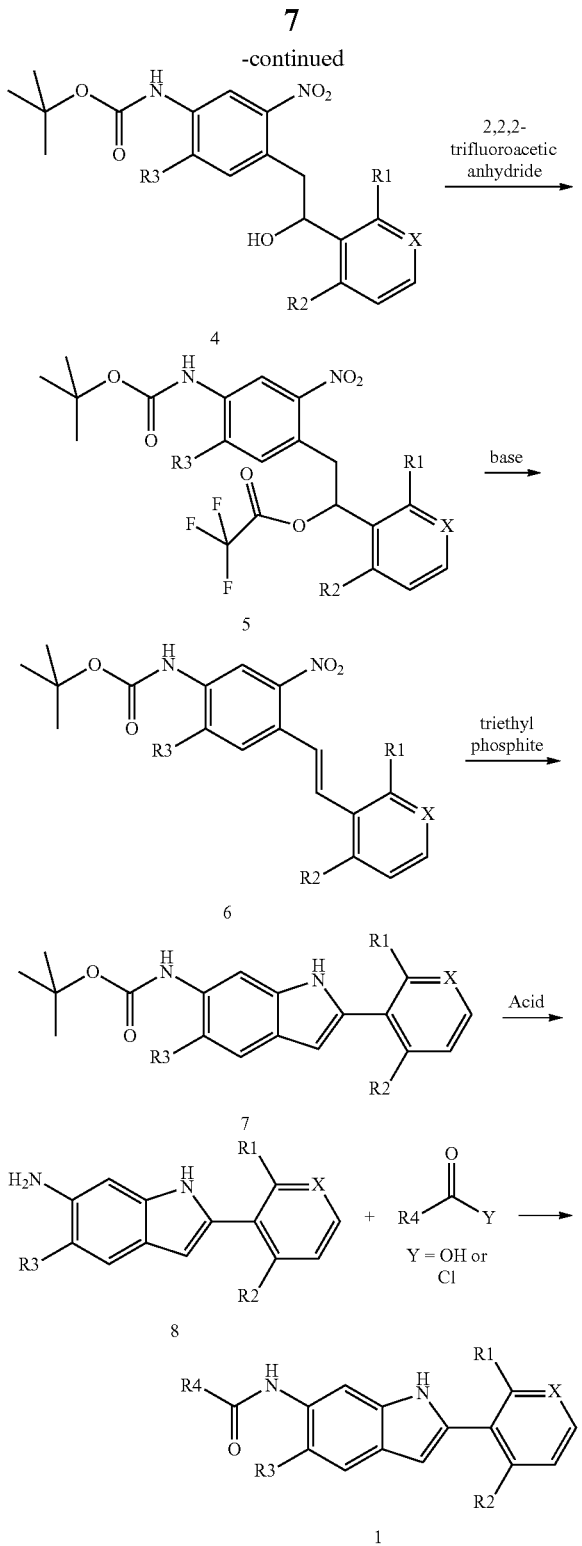

a skilled artisan to afford (3-nitro-4-trimethylsilanylmethyl-phenyl)-carbamic acid tert-butyl ester 3. Tetra-butylammonium fluoride can then be added to a solution of ester 3 and 4-iodo-2-methoxynicotinaldehyde in THF to afford {4-[2-hydroxy-2-(4-iodo-2-methoxy-pyridin-3-yl)-ethyl]-3-nitro-phenyl}-carbamic acid tert-butyl ester 4. A solution of compound 4, in turn, can be added to 2,2,2-trifluoroacetic anhydride and allowed to react to afford trifluoro-acetic acid 2-(4-tert-butoxycarbonyl-amino-2-nitro-phenyl)-1-(4-iodo-2-methoxy-pyridin-3-yl)-ethyl ester 5.

A solution of crude trifluoro-acetic acid 2-(4-tert-butoxycarbonyl-amino-2-nitro-phenyl)-1-(4-iodo-2-methoxy-pyridin-3-yl)-ethyl ester 5 in THF can then be added to 8-diazabicyclo[5.4.0]undec-7-ene. After allowing to react, extracting the aqueous phase, washing the organing layers, filtration, concentration and chromatography, {4-[(E)-2-(4-iodo-2-methoxy-pyridin-3-yl)-vinyl]-3-nitro-phenyl}-carbamic acid tert-butyl ester 6 can be provided. Refluxing a solution of 6 with triethyl phosphite, followed by known separation steps can afford [2-(4-iodo-2-methoxy-pyridin-3-yl)-1H-indol-6-yl]-carbamic acid tert-butyl ester 7.

A solution of [2-(4-iodo-2-methoxy-pyridin-3-yl)-1H-indol-6-yl]-carbamic acid tert-butyl ester 7 can be added to an acid such as 2,2,2-trifluoroacetic acid to afford compound 8. Addition of an anhydride, such as 2,2,2-trifluoroacetic anhydride, to compound 8, followed with extraction, filtration and separation steps known in the art can afford compound 1, wherein the R groups and X can be those as described, for example, in the Examples and claims below.

The invention will now be illustrated by the following examples which have no limiting character.

EXAMPLES

Although certain exemplary embodiments are depicted and described herein, the compounds of the present invention can be prepared using appropriate starting materials according to the methods described generally herein and/or by methods available to one of ordinary skill in the art.

Intermediates and final compounds were purified by either flash chromatography and/or by reverse-phase preparative HPLC (high performance liquid chromatography). Unless otherwise noted, flash chromatography was performed using (1) the Biotage SP1™ system and the Quad 12/25 Cartridge module (from Biotage AB), (2) the ISCO CombiFlash® chromatography instrument (from Teledyne Isco, Inc.), or (3) an Analogix® IntelliFlash280™ chromatography instrument (from Analogix Inc., a subsidiary of Varian Inc.). Unless otherwise noted, the silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Reverse-phase preparative HPLC was performed using a Waters® Delta-Prep™ 3000 HPLC system from Waters Corporation using one or more of the following columns: a Varian Pursuit® C-18 column (10 μm, 20×150 mm) from Varian, Inc., an Xbridge™ Prep $C_{18}$ column (5 μm, OBD™ 20×100 mm) from Waters Corporation, or a SunFire™ Prep $C_{18}$ column (5 μm, OBD™ 30×100 mm) from Waters Corporation.

Mass spectrometry (MS) or high resolution mass spectrometry (HRMS) was performed using a Waters® ZQ™ 4000 (from Waters Corporation), a Waters® Quattro micro™ API (from Waters Corporation), a Micromass® Platform II (from Micromass, a division of Waters Corporation), a Bruker® Apex®II FTICR with a 4.7 Tesla magnet (from As seen in Scheme 1, compound 2 can be made by reacting 3-nitroanaline and di-tert-dicarbonate in the presence of a catalyst, such as pyridine-4-ylamine, and a solvent, such as THF.

The resultant (3-nitro-phenyl)-carbamic acid tert-butyl ester 2 can then be placed into solution with THF and reacted with ((trimethylsilyl)methyl)magnesiumchloride. A solution of 2,3-dichloro-5,6-dicyano-1,4-benzoquinone in THF can then be added and allowed to react under conditions known to Bruker Corporation), a Waters® Alliance® 2795-ZQ™2000 (from Waters Corporation), or an MDS Sciex™ API-2000™n API (from MDS Inc.). Mass spectra data generally only indicates the parent ions unless otherwise stated. MS or HRMS data is provided for a particular intermediate or compound where indicated.

Nuclear magnetic resonance spectroscopy (NMR) was performed using a Varian® Mercury300 NMR spectrometer (for the $^1$H NMR spectra acquired at 300 MHz) and a Varian® Inova400 NMR spectrometer (for the $^1$H NMR spectra acquired at 400 MHz) both from Varian Inc. NMR data is provided for a particular intermediate or compound where indicated.

All reactions involving air-sensitive reagents were performed under an inert atmosphere. Reagents were used as received from commercial suppliers unless otherwise noted.

Example 1

[2-(4-Iodo-2-methoxy-pyridin-3-yl)-1H-indol-6-yl]-carbamic acid tert-butyl ester

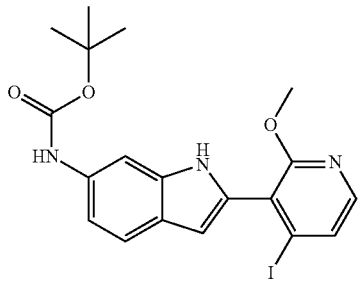 [SMILES: COc1nccc(I)c1-c1cc2ccc(NC(=O)OC(C)(C)C)cc2[nH]1]

A solution of 3-nitroaniline (5.00 g, 36.2 mmol), di-tert-butyl dicarbonate (7.90 g, 36.2 mmol) and pyridine-4-ylamine (3.75 g, 39.8 mmol) in THF (50 mL) was stirred at 25° C. for 3 h. The reaction mixture was concentrated in vacuo, then added ethyl acetate (50 mL). The organic solution was washed three times with water and once with brine. The organic layer was then dried over magnesium sulfate, filtered and concentrated in vacuo. Flash chromatography (80/20 hexanes/ethyl acetate) afforded (3-nitro-phenyl)-carbamic acid tert-butyl ester (7.00 g, 81%) as an oil.

A solution of (3-nitro-phenyl)-carbamic acid tert-butyl ester (1.20 g, 5.04 mmol) in THF (50 mL) was added ((trimethylsilyl)methyl)magnesium chloride (1.48 g, 10.1 mmol) at −70° C. under nitrogen gas. The solution was then stirred at −70° C. for one h. A solution of 2,3-dichloro-5,6-dicyano-1,4-benzoquinone (2.74 g, 12.1 mmol) in THF (30 mL) was added, the reaction was warmed to 0° C. and the reaction was allowed to stir at 0° C. for another hour. The reaction mixture is poured into an aqueous solution of acetic acid (50 mL, 5%v/v) and the aqueous phase was extracted three times with ethyl acetate. The combined organic layers were washed with brine and dried over magnesium sulfate. Filtration followed by concentration in vacuo gave a brown oil. Flash chromatography (80/20 hexanes/ethyl acetate) afforded (3-nitro-4-trimethylsilanylmethyl-phenyl)-carbamic acid tert-butyl ester (1.20 g, 73%) as a light oil.

A solution of (3-nitro-4-trimethylsilanylmethyl-phenyl)-carbamic acid tert-butyl ester (1.00 g, 3.08 mmol) and 4-iodo-2-methoxynicotinaldehyde (811 mg, 3.08 mmol, Eq: 1.00) in THF (10 mL) was added tetra-butylammonium fluoride (121 mg, 462 µmol) at 25° C., the color of the solution changed to dark blue after the addition. The reaction mixture was stirred at 25° C. for 30 min. The solution of crude {4-[2-hydroxy-2-(4-iodo-2-methoxy-pyridin-3-yl)-ethyl]-3-nitro-phenyl}-carbamic acid tert-butyl ester (crude 1.59 g, 3.08 mmol) was used directly for next step. M+H 515.9.

A solution of crude {4-[2-hydroxy-2-(4-iodo-2-methoxy-pyridin-3-yl)-ethyl]-3-nitro-phenyl}-carbamic acid tert-butyl ester (crude 1.59 g, 3.08 mmol) in THF (10 mL) was added 2,2,2-trifluoroacetic anhydride (734 mg, 3.49 mmol) at 25° C., the color changed to dark blue. The reaction was allowed to stir at 25° C. for 30 min. The solution of crude trifluoro-acetic acid 2-(4-tert-butoxycarbonyl-amino-2-nitro-phenyl)-1-(4-iodo-2-methoxy-pyridin-3-yl)-ethyl ester (crude 1.88 g, 2.91 mmol) was used directly for next step. MH+ 611.

A solution of crude trifluoro-acetic acid 2-(4-tert-butoxycarbonyl-amino-2-nitro-phenyl)-1-(4-iodo-2-methoxy-pyridin-3-yl)-ethyl ester (crude 1.88 g, 3.08 mmol) in THF (10 mL) was added 8-diazabicyclo[5.4.0]undec-7-ene (1.33 g, 8.74 mmol) at 25° C. The reaction was allowed to stir at 70° C. for 3 hours. The reaction mixture was cooled to 25° C., and poured into water. The aqueous phase was extracted three times with ethyl acetate. The combined organic layers were washed with brine and dried over magnesium sulfate. Filtration followed by concentration in vacuo gave a brown solid. Flash chromatography (80/20 hexanes/ethyl acetate) afforded {4-[(E)-2-(4-iodo-2-methoxy-pyridin-3-yl)-vinyl]-3-nitro-phenyl}-carbamic acid tert-butyl ester (850 mg, 55%) as an oil. MH+ 497.9.

A solution of {4-[(E)-2-(4-iodo-2-methoxy-pyridin-3-yl)-vinyl]-3-nitro-phenyl}-carbamic acid tert-butyl ester (800 mg, 1.61 mmol) in triethyl phosphite (16.0 ml) was refluxed for 3 h. The reaction mixture was cooled to 25° C. and poured into water and the aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded [2-(4-iodo-2-methoxy-pyridin-3-yl)-1H-indol-6-yl]-carbamic acid tert-butyl ester (250 mg, 33%) as a white solid. MH+ 465.9.

Example 2

2,2,2-Trifluoro-N-[2-(4-iodo-2-methoxy-pyridin-3-yl)-1H-indol-6-yl]-acetamide

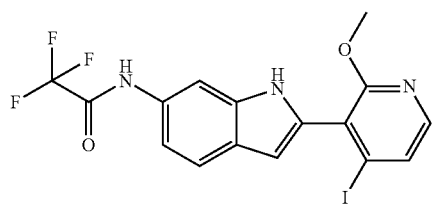 [SMILES: COc1nccc(I)c1-c1cc2ccc(NC(=O)C(F)(F)F)cc2[nH]1]

A solution of [2-(4-iodo-2-methoxy-pyridin-3-yl)-1H-indol-6-yl]-carbamic acid tert-butyl ester (90 mg, 0.19 mmol) in CH$_2$Cl$_2$ (5 mL) was added 2,2,2-trifluoroacetic acid (0.5 mL) at 25° C. The solution was heated to reflux for 3 h. Concentrate the solution in vacuo to afford crude 2-(4-iodo-2-methoxy-pyridin-3-yl)-1H-indol-6-ylamine (65 mg, 92%) as light yellow oil. The crude product was used directly for next step. MH+ 365.9.

A solution of crude 2-(4-iodo-2-methoxy-pyridin-3-yl)-1H-indol-6-ylamine (65 mg, 0.18 mmol) in CH$_2$Cl$_2$ (5 mL)

was added 2,2,2-trifluoroacetic anhydride (187 mg, 0.89 mmol) followed by triethylamine (180 mg, 1.78 mmol). The solution was stirred at 25° C. for 1 hour, and poured into water. The aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded 2,2,2-trifluoro-N-[2-(4-iodo-2-methoxy-pyridin-3-yl)-1H-indol-6-yl]-acetamide (48 mg, 59%) as a white solid. MH+ 461.8.

Example 3

2,2-Difluoro-N-[2-(4-iodo-2-methoxy-pyridin-3-yl)-1H-indol-6-yl]-acetamide

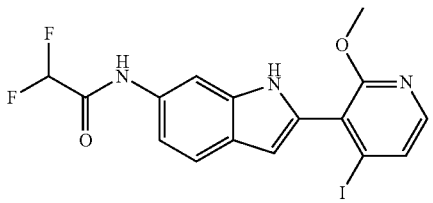 [SMILES: COc1nccc(I)c1-c1cc2ccc(NC(=O)C(F)F)cc2[nH]1]

A solution of 2-(4-iodo-2-methoxy-pyridin-3-yl)-1H-indol-6-ylamine (30 mg, 0.08 mmol) in $CH_2Cl_2$ (5 mL) was added 2,2-difluoroacetic acid (12 mg, 0.12 mmol) and HATU (47 mg, 0.12 mol). The solution was stirred at 25° C. for 1 h and poured into water. The aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded 2,2-difluoro-N-[2-(4-iodo-2-methoxy-pyridin-3-yl)-1H-indol-6-yl]-acetamide (24 mg, 67%) as a white solid. MH+ 443.9.

Example 4

N-[2-(4-Chloro-2-methoxy-pyridin-3-yl)-1H-indol-6-yl]-2,2,2-trifluoro-acetamide

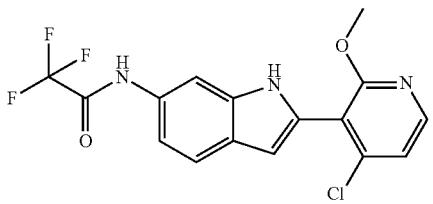 [SMILES: COc1nccc(Cl)c1-c1cc2ccc(NC(=O)C(F)(F)F)cc2[nH]1]

A solution of (3-nitro-4-trimethylsilanylmethyl-phenyl)-carbamic acid tert-butyl ester (1.00 g, 3.08 mmol) and 4-chloro-2-methoxynicotinaldehyde (529 mg, 3.08 mmol) in THF (10 mL) was added tetra-butylammonium fluoride (121 mg, 462 μmol) at 25° C., the color of the solution changed to dark blue after the addition. The reaction mixture was stirred at 25° C. for 30 min. The solution of crude {4-[2-(4-chloro-2-methoxy-pyridin-3-yl)-2-hydroxy-ethyl]-3-nitro-phenyl}-carbamic acid tert-butyl ester (crude 1.30 g, 3.08 mmol) was used directly for next step.

A solution of {4-[2-(4-chloro-2-methoxy-pyridin-3-yl)-2-hydroxy-ethyl]-3-nitro-phenyl}-carbamic acid tert-butyl ester (crude 1.30 g, 3.08 mmol) in THF (10 mL) was added 2,2,2-trifluoroacetic anhydride (734 mg, 3.49 mmol) at 25° C., the color changed to dark blue. The reaction was allowed to stir at 25° C. for 30 min. The solution of trifluoro-acetic acid 2-(4-tert-butoxycarbonylamino-2-nitro-phenyl)-1-(4-chloro-2-methoxy-pyridin-3-yl)-ethyl ester (crude 1.60 g, 3.08 mmol) was used directly for next step.

A solution of trifluoro-acetic acid 2-(4-tert-butoxycarbonylamino-2-nitro-phenyl)-1-(4-chloro-2-methoxy-pyridin-3-yl)-ethyl ester (crude 1.60 g, 3.08 mmol) in THF (10 mL) was added 8-diazabicyclo[5.4.0]undec-7-ene (1.33 g, 8,74 mmol) at 25° C. The reaction was allowed to stir at 70° C. for 3 hours. The reaction mixture was cooled to 25° C., and poured into water. The aqueous phase was extracted three times with ethyl acetate. The combined organic layers were washed with brine and dried over magnesium sulfate. Filtration followed by concentration in vacuo gave a brown solid. Flash chromatography (80/20 hexanes/ethyl acetate) afforded {4-[(E)-2-(4-chloro-2-methoxy-pyridin-3-yl)-vinyl]-3-nitro-phenyl}-carbamic acid tert-butyl ester (800 mg, 68%) as an oil. MH+ 406.0.

A solution of {4-[(E)-2-(4-chloro-2-methoxy-pyridin-3-yl)-vinyl]-3-nitro-phenyl}-carbamic acid tert-butyl ester (800 mg, 1.97 mmol) in triethyl phosphite (16.0 ml) was refluxed for 3 hours. The reaction mixture was cooled to 25° C., and poured into water. The aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded [2-(4-chloro-2-methoxy-pyridin-3-yl)-1H-indol-6-yl]-carbamic acid tert-butyl ester (180 mg, 33%) as a white solid. MH+ 374.0.

A solution of [2-(4-chloro-2-methoxy-pyridin-3-yl)-1H-indol-6-yl]-carbamic acid tert-butyl ester (160 mg, 0.43) in $CH_2Cl_2$ (5 mL) was added 2,2,2-trifluoroacetic acid (0.5 mL) at 25° C. The solution was heated to reflux for 3 hours. Concentrate the solution in vacuo to afford crude 2-(4-chloro-2-methoxy-pyridin-3-yl)-1H-indol-6-ylamine (105 mg, 90%) as light yellow oil. The crude product was used directly for next step. MH+ 273.9.

A solution of crude 2-(4-chloro-2-methoxy-pyridin-3-yl)-1H-indol-6-ylamine (30 mg, 0.11 mmol) in $CH_2Cl_2$ (5 mL) was added 2,2,2-trifluoroacetic anhydride (115 mg, 0.55 mmol) followed by triethylamine (111 mg, 1.1 mmol). The solution was stirred at 25° C. for 1 h and poured into water. The aqueous phase was extracted three times with ethyl acetate and the combined organic layers were washed with brine and dried over magnesium sulfate. Filtration followed by concentration in vacuo gave a brown solid. Flash chromatography (70/30 hexanes/ethyl acetate) afforded N-[2-(4-chloro-2-methoxy-pyridin-3-yl)-1H-indol-6-yl]-2,2,2-trifluoro-acetamide (18 mg, 43%) as a white solid. MH+ 370.0.

Example 5

[2-(4-Iodo-2-methoxy-pyridin-3-yl)-1H-indol-6-yl]-methyl-amine

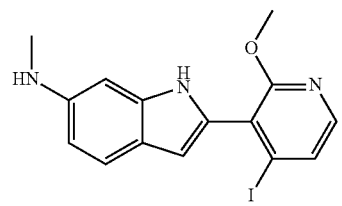 [SMILES: CNc1ccc2cc(-c3c(I)ccnc3OC)[nH]c2c1]

A solution of N-methyl-3-nitroaniline (1.00 g, 6.57 mmol), di-tert-butyl dicarbonate (1.43 g, 6.57 mmol) and pyridine- 4-ylamine (619 mg, 6.57 mmol) in THF (50 mL) was stirred at 25° C. for 3 h. The reaction mixture was concentrated in vacuo, then added ethyl acetate (50 mL). The organic solution was washed three times with water and once with brine. The organic layer was then dried over magnesium sulfate, filtered and concentrated in vacuo. Flash chromatography (80/20 hexanes/ethyl acetate) afforded methyl-(3-nitro-phenyl)-carbamic acid tert-butyl ester (1.60g, 97%) as an oil.

A solution of methyl-(3-nitro-phenyl)-carbamic acid tert-butyl ester (1.60 g, 6.34 mmol) in THF (50 mL) was added ((trimethylsilyl)methyl)magnesium chloride (1.40 g, 10.1 mmol) at −70° C. under nitrogen gas The solution was then stirred at −70° C. for one hour.

A solution of 2,3-dichloro-5,6-dicyano-1,4-benzoquinone (1.73 g, 7.61 mmol) in THF (30 mL) was added, the reaction was warmed to 0° C. and allowed to stir at 0° C. for another hour. The reaction mixture is poured into an aqueous solution of acetic acid (50 mL, 5%). The aqueous phase was extracted three times with ethyl acetate. The combined organic layers were washed with brine and dried over magnesium sulfate. Filtration followed by concentration in vacuo gave brown oil. Flash chromatography (80/20 hexanes/ethyl acetate) afforded methyl-(3-nitro-4-trimethylsilanylmethyl-phenyl)-carbamic acid tert-butyl ester (0.80 g, 37%) as a light oil.

To a solution of methyl-(3-nitro-4-trimethylsilanylmethyl-phenyl)-carbamic acid tert-butyl ester (0.75 g, 1.10 mmol) and 4-iodo-2-methoxynicotinaldehyde (1.17 g, 4.43 mmol) in THF (10 mL) was added tetra-butylammonium fluoride (174 mg, 665 μmol) at 25° C. Upon addition, the color of the solution changed to dark blue. The reaction mixture was stirred at 25° C. for 30 min.

To the reaction mixture was then added 2,2,2-trifluoroacetic anhydride (1.37 g, 6.52 mmol) at 25° C. resulting in a color change to dark blue. The reaction was allowed to stir at 25° C. for 30 min.

To the reaction mixture was then added 8-diazabicyclo [5.4.0]undec-7-ene (1.64 g, 10.8 mmol) at 25° C. The reaction was allowed to stir at 70° C. for 3 h. The reaction mixture was cooled to 25° C. and poured into water. The aqueous phase was extracted three times with ethyl acetate. The combined organic layers were washed with brine and dried over magnesium sulfate. Filtration followed by concentration in vacuo gave a brown solid. Flash chromatography (80/20 hexanes/ethyl acetate) afforded {4-[(E)-2-(4-iodo-2-methoxy-pyridin-3-yl)-vinyl]-3-nitro-phenyl}-methyl-carbamic acid tert-butyl ester (1.0 g, 91%) as an oil. MH+ 512.0.

A solution of {4-[(E)-2-(4-iodo-2-methoxy-pyridin-3-yl)-vinyl]-3-nitro-phenyl}-methyl-carbamic acid tert-butyl ester (1.00 g, 1.96 mmol) in triethyl phosphite (5.0 ml) was refluxed for 3 h. The reaction mixture was cooled to 25° C., and poured into water. The aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded [2-(4-iodo-2-methoxy-pyridin-3-yl)-1H-indol-6-yl]-methyl-carbamic acid tert-butyl ester (550 mg, 59%) as a white solid. MH+ 479.7.

A solution of [2-(4-iodo-2-methoxy-pyridin-3-yl)-1H-indol-6-yl]-methyl-carbamic acid tert-butyl ester (520 mg, 1.08 mmol) in CH$_2$Cl$_2$ (5 mL) was added 2,2,2-trifluoroacetic acid (1 mL) at 25° C. The solution was heated to reflux for 3 h. The solution was concentrated in vacuo and poured into water. The aqueous phase was extracted three times with ethyl acetate and the combined organic layers were washed with brine and dried over magnesium sulfate. Filtration followed by concentration in vacuo gave a brown solid. Flash chromatography (70/30 hexanes/ethyl acetate) afforded [2-(4-iodo-2-methoxy-pyridin-3-yl)-1H-indol-6-yl]-methyl-amine (380 mg, 92%) as a white product. MH+ 379.9.

Example 6

2,2-Difluoro-N-[2-(4-iodo-2-methoxy-pyridin-3-yl)-1H-indol-6-yl]-N-methyl-acetamide

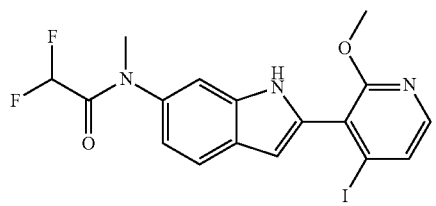 [SMILES: COc1nccc(I)c1-c1cc2ccc(N(C)C(=O)C(F)F)cc2[nH]1]

A solution of [2-(4-iodo-2-methoxy-pyridin-3-yl)-1H-indol-6-yl]-methyl-amine (30 mg, 0.08 mmol) in CH$_2$Cl$_2$ (5 mL) was added 2,2-difluoroacetic acid (11 mg, 0.12 mmol) and HATU (45 mg, 0.12 mol). The solution was stirred at 25° C. for 1 h and poured into water. The aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded 2,2-difluoro-N-[2-(4-iodo-2-methoxy-pyridin-3-yl)-1H-indol-6-yl]-N-methyl-acetamide (12 mg, 33%) as a white solid. MH+ 457.8.

Example 7

N-[2-(4-Iodo-2-methoxy-pyridin-3-yl)-1H-indol-6-yl]-N-methyl-acetamide

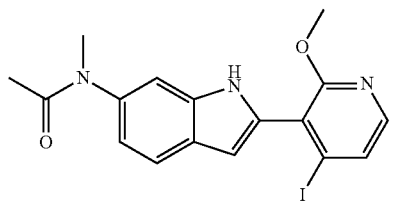 [SMILES: COc1nccc(I)c1-c1cc2ccc(N(C)C(C)=O)cc2[nH]1]

A solution of [2-(4-iodo-2-methoxy-pyridin-3-yl)-1H-indol-6-yl]-methyl-amine (30 mg, 0.08 mmol) in CH$_2$Cl$_2$ (5 mL) was added acetic anhydride (8 mg, 0.08 mmol) and triethylamine (80 mg, 0.791 mol). The solution was stirred at 25° C. for 1 h and poured into water. The aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded N-[2-(4-iodo-2-methoxy-pyridin-3-yl)-1H-indol-6-yl]-N-methyl-acetamide (18 mg, 53%) as a white solid. MH+ 422.0.

Example 8

2-(4-Iodo-2-methoxy-pyridin-3-yl)-5-methoxy-1H-indol-6-ylamine

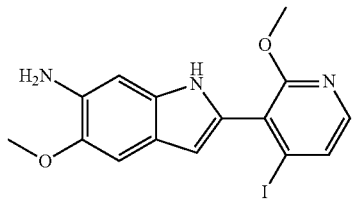 [SMILES: COc1cc2cc(-c3c(I)ccnc3OC)[nH]c2cc1N]

A solution of 2-methoxy-5-nitroaniline (3.00 g, 17.8 mmol), di-tert-butyl dicarbonate (3.89 g, 17.8 mmol) and pyridine-4-ylamine (1.68 g, 17.8 mmol) in THF (50 mL) was stirred at 25° C. for 3 h. The reaction mixture was concentrated in vacuo then diluted with ethyl acetate (50 mL). The organic solution was washed three times with water and once with brine. The organic layer was then dried over magnesium sulfate, filtered and concentrated in vacuo. Flash chromatography (80/20 hexanes/ethyl acetate) afforded (2-methoxy-5-nitro-phenyl)-carbamic acid tert-butyl ester (3.80 g, 79%) as an oil.

A solution of (2-methoxy-5-nitro-phenyl)-carbamic acid tert-butyl ester (1.80 g, 6.71 mmol) in THF (50 mL) was added ((trimethylsilyl)methyl)magnesium chloride (2.47 g, 16.8 mmol) at −70° C. under nitrogen gas. The solution was then stirred at −70° C. for one hour. A solution of 2,3-dichloro-5,6-dicyano-1,4-benzoquinone (3.05 g, 13.4 mmol) in THF (30 mL) was added, the reaction was warmed to 0° C. The reaction was allowed to stir at 0° C. for another hour. The reaction mixture is poured into an aqueous solution of acetic acid (50 mL, 5%). The aqueous phase was extracted three times with ethyl acetate and the combined organic layers were washed with brine and dried over magnesium sulfate. Filtration followed by concentration in vacuo gave brown oil. Flash chromatography (80/20 hexanes/ethyl acetate) afforded (2-methoxy-5-nitro-4-trimethylsilanylmethyl-phenyl)-carbamic acid tert-butyl ester (1.50 g, 63%) as a light oil.

A solution of (2-methoxy-5-nitro-4-trimethylsilanylmethyl-phenyl)-carbamic acid tert-butyl ester (0.75 g, 2.12 mmol) and 4-iodo-2-methoxynicotinaldehyde (557 mg, 2.12 mmol) in THF (10 mL) was added tetra-butyl ammonium fluoride (83 mg, 317 µmol) at 25° C., the color of the solution changed to dark blue after the addition. The reaction mixture was stirred at 25° C. for 30 min. The solution of crude {4-[2-hydroxy-2-(4-iodo-2-methoxy-pyridin-3-yl)-ethyl]-2-methoxy-5-nitro-phenyl}-carbamic acid tert-butyl ester (crude 1.18 g, 2.12 mmol) was used directly for next step. M+H 546.0.

A solution of crude {4-[2-hydroxy-2-(4-iodo-2-methoxy-pyridin-3-yl)-ethyl]-2-methoxy-5-nitro-phenyl}-carbamic acid tert-butyl ester (crude 1.18 g, 2.12 mmol) in THF (10 mL) was added 2,2,2-trifluoroacetic anhydride (1.27 g, 6.05 mmol) at 25° C., the color changed to dark blue. The reaction was allowed to stir at 25° C. for 30 min. The solution of crude trifluoro-acetic acid 2-(4-tert-butoxycarbonylamino-5-methoxy-2-nitro-phenyl)-1-(4-iodo-2-methoxy-pyridin-3-yl)-ethyl ester (crude 1.35 g, 2.12 mmol) was used directly for next step. MH+ 641.9.

A solution of crude trifluoro-acetic acid 2-(4-tert-butoxycarbonylamino-5-methoxy-2-nitro-phenyl)-1-(4-iodo-2-methoxy-pyridin-3-yl)-ethyl ester (crude 1.35 g, 2.12 mmol) in THF (10 mL) was added 8-diazabicyclo[5.4.0]undec-7-ene (1.48 g, 9.75 mmol) at 25° C. The reaction was allowed to stir at 70° C. for 3 h, cooled to 25° C. and poured into water. The aqueous phase was extracted three times with ethyl acetate. The combined organic layers were washed with brine and dried over magnesium sulfate. Filtration followed by concentration in vacuo gave a brown solid. Flash chromatography (80/20 hexanes/ethyl acetate) afforded {4-[(E)-2-(4-iodo-2-methoxy-pyridin-3-yl)-vinyl]-2-methoxy-5-nitrophenyl}-carbamic acid tert-butyl ester (560 mg, 55%) as an oil. MH+ 527.8.

A solution of {4-[(E)-2-(4-iodo-2-methoxy-pyridin-3-yl)-vinyl]-2-methoxy-5-nitro-phenyl}-carbamic acid tert-butyl ester (560 mg, 1.06 mmol) in triethyl phosphite (5.0 ml) was refluxed for 3 h, cooled to 25° C. and poured into water. The aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded [2-(4-iodo-2-methoxy-pyridin-3-yl)-5-methoxy-1H-indol-6-yl]-carbamic acid tert-butyl ester (250 mg, 48%) as a white solid. MH+ 496.0.

A solution of [2-(4-iodo-2-methoxy-pyridin-3-yl)-5-methoxy-1H-indol-6-yl]-carbamic acid tert-butyl ester (250 mg, 0.51 mmol) in CH$_2$Cl$_2$ (5 mL) was added 2,2,2-trifluoroacetic acid (1 mL) at 25° C. The solution was heated to reflux for 3 h and then concentrated in vacuo and poured into water. The aqueous phase was extracted three times with ethyl acetate. The combined organic layers were washed with brine and dried over magnesium sulfate. Filtration followed by concentration in vacuo gave a brown solid. Flash chromatography (50/50 hexanes/ethyl acetate) afforded 2-(4-iodo-2-methoxy-pyridin-3-yl)-5-methoxy-1H-indol-6-ylamine (170 mg, 85%) as a white solid. MH+ 395.0.

Example 9

2-(2-Chloro-6-methoxy-phenyl)-1H-indol-6-ylamine

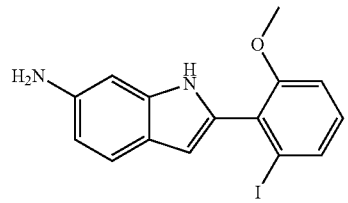 [SMILES: COc1cccc(I)c1-c1cc2ccc(N)cc2[nH]1]

A solution of (3-nitro-4-trimethylsilanylmethyl-phenyl)-carbamic acid tert-butyl ester (1.00 g, 3.08 mmol) and 2-chloro-6-methoxybenzaldehyde (526 mg, 3.08 mmol) in THF (10 mL) was added tetra-butylammonium fluoride (121 mg, 462 µmol) at 25° C., the color of the solution changed to dark blue after the addition. The reaction mixture was stirred at 25° C. for 30 min and poured into water. The aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded {4-[2-(2-chloro-6-methoxy-phenyl)-2-hydroxy-ethyl]-3-nitro-phenyl}-carbamic acid tert-butyl ester (0.45 g, 35%) as an oil.

To a solution of {4-[2-(2-chloro-6-methoxy-phenyl)-2-hydroxy-ethyl]-3-nitro-phenyl}-carbamic acid tert-butyl ester (0.45 g, 1.06 mmol) in THF (10 mL) was added 2,2,2-trifluoroacetic anhydride (671 mg, 3.18 mmol) at 25° C. resulting in a color change to dark blue. The reaction was allowed to stir at 25° C. for 30 min after which 8-diazabicyclo[5.4.0]undec-7-ene (0.76 g, 5.00 mmol) was added. The reaction was heated to 70° C. for 3 h and then cooled to 25° C. and poured into water. The aqueous phase was extracted three times with ethyl acetate. The combined organic layers were washed with brine and dried over magnesium sulfate. Filtration followed by concentration in vacuo gave a brown solid. Flash chromatography (90/10 hexanes/ethyl acetate) afforded {4-[(E)-2-

(2-chloro-6-methoxy-phenyl)-vinyl]-3-nitro-phenyl}-carbamic acid tert-butyl ester (240 mg, 60%) as an oil.

A solution of {4-[(E)-2-(2-chloro-6-methoxy-phenyl)-vinyl]-3-nitro-phenyl}-carbamic acid tert-butyl ester (240 mg, 0.59 mmol) in triethyl phosphite (5.0 ml) was refluxed for 3 h. The reaction mixture was cooled to 25° C., and poured into water. The aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded [2-(2-chloro-6-methoxy-phenyl)-1H-indol-6-yl]-carbamic acid tert-butyl ester (140 mg, 63%) as a white solid. MH+ 373.0.

A solution of [2-(2-chloro-6-methoxy-phenyl)-1H-indol-6-yl]-carbamic acid tert-butyl ester (120 mg, 0.32 mmol) in CH$_2$Cl$_2$ (5 mL) was added 2,2,2-trifluoroacetic acid (0.5 mL) at 25° C. The solution was heated to reflux for 3 h, concentrated and poured into water. The aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded 2-(2-chloro-6-methoxy-phenyl)-1H-indol-6-ylamine (80 mg, 91%) as a white solid. MH+ 272.9.

Example 10

N-[2-(2-Chloro-6-methoxy-phenyl)-1H-indol-6-yl]-2,2,2-trifluoro-acetamide

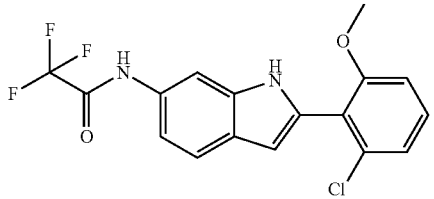 [SMILES: COc1cccc(Cl)c1-c1cc2ccc(NC(=O)C(F)(F)F)cc2[nH]1]

To a solution of 2-(2-chloro-6-methoxy-phenyl)-1H-indol-6-ylamine (50 mg, 0.18 mmol) in CH$_2$Cl$_2$ (5 mL) was added 2,2,2-trifluoroacetic anhydride (193 mg, 0.92 mmol) followed by triethylamine (186 mg, 1.8 mmol). The solution was stirred at 25° C. for 1 h and poured into water. The aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded N-[2-(2-chloro-6-methoxy-phenyl)-1H-indol-6-yl]-2,2,2-trifluoro-acetamide (38 mg, 56%) as a white solid. MH+ 369.0.

Example 11

3-Chloro-N-[2-(4-iodo-2-methoxy-pyridin-3-yl)-1H-indol-6-yl]-benzamide

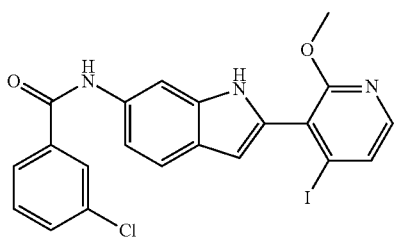 [SMILES: COc1nccc(I)c1-c1cc2ccc(NC(=O)c3cccc(Cl)c3)cc2[nH]1]

To a solution of 2-(4-iodo-2-methoxy-pyridin-3-yl)-1H-indol-6-ylamine (50 mg, 0.14 mmol) in CH$_2$Cl$_2$ (5 mL) was added 3-chlorobenzoic acid (21 mg, 0.14 mmol) and HATU (52 mg, 0.14 mol). The solution was stirred at 25° C. for 1 h and poured into water. The aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded 3-chloro-N-[2-(4-iodo-2-methoxy-pyridin-3-yl)-1H-indol-6-yl]-benzamide (56 mg, 81%) as a white solid. MH+ 503.8.

Example 12

3-Chloro-N-[2-(4-chloro-2-methoxy-pyridin-3-yl)-1H-indol-6-yl]-benzamide

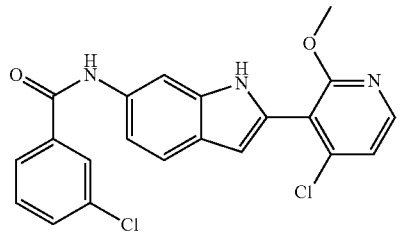 [SMILES: COc1nccc(Cl)c1-c1cc2ccc(NC(=O)c3cccc(Cl)c3)cc2[nH]1]

To a solution of 2-(4-chloro-2-methoxy-pyridin-3-yl)-1H-indol-6-ylamine (30 mg, 0.11 mmol) in CH$_2$Cl$_2$ (5 mL) was added 3-chlorobenzoic acid (17 mg, 0.11 mmol) and HATU (42 mg, 0.11 mol). The solution was stirred at 25° C. for 1 h and poured into water. The aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded 3-chloro-N-[2-(4-chloro-2-methoxy-pyridin-3-yl)-1H-indol-6-yl]-benzamide (35 mg, 78%) as a white solid. MH+ 411.9.

Example 13

(S)-1-(4-Fluoro-benzenesulfonyl)-piperidine-2-carboxylic acid[2-(4-chloro-2-methoxy-pyridin-3-yl)-1H-indol-6-yl]amide

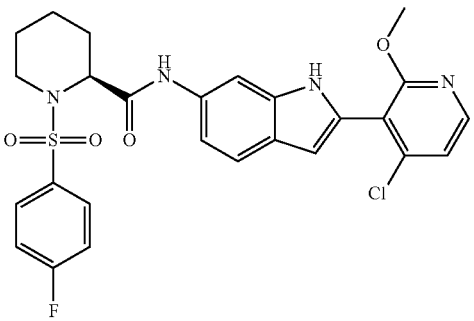 [SMILES: COc1nccc(Cl)c1-c1cc2ccc(NC(=O)[C@@H]3CCCCN3S(=O)(=O)c3ccc(F)cc3)cc2[nH]1]

To a solution of 2-(4-chloro-2-methoxy-pyridin-3-yl)-1H-indol-6-ylamine (35 mg, 0.13 mmol) in CH$_2$Cl$_2$ (5 mL) was added (S)-1-(4-fluoro-benzenesulfonyl)-piperidine-2-carboxylic acid (37 mg, 0.13 mmol) and HATU (49 mg, 0.13 mol). The solution was stirred at 25° C. for 1 h and poured into water. The aqueous phase was extracted three times with ethyl acetate. The combined organic layers were washed with brine and dried over magnesium sulfate. Filtration followed by concentration in vacuo gave a brown solid. Flash chromatography (70/30 hexanes/ethyl acetate) afforded (S)-1-(4-fluorobenzenesulfonyl)-piperidine-2-carboxylic acid[2-(4-chloro-2-methoxy-pyridin-3-yl)-1H-indol-6-yl]-amide (60 mg, 86%) as a white solid. MH+ 543.0.

Example 14

IC$_{50}$ Determination

Dose Response Assay: ChanTest hTRPA1-CHO Stably Transfected Cell Line
Cell Culture and Assay Reagents:

| | |
|---|---|
| Ham's F12 | (GIBCO #11765-047) |
| Tetracycline-free Fetal Bovine Serum | (ClonTech#631106, Lot A301097018) |
| Blasticidin (10 mg/ml stock) | (GIBCO #A11139-02) |
| Zeocin (100 mg/ml stock) | (GIBCO #R250-01) |
| Doxycycline | (SIGMA #D9891) |
| Penicillin-Sprepromycin solution (100X) | (GIBCO #15140-122) |
| GlutaMAX (100X) | (GIBCO #35050) |
| Trypsin-EDTA | (GIBCO #25200-056) |
| PBS (without Calcium and Magnesium) | (GIBCO #14190) |
| HBSS | (GIBCO #14025) |
| Hepes | (GIBCO #15630) |
| BSA (fatty acid free, low endotoxin) | (SIGMA #A8806-5G) |
| DMSO | (SIGMA #D2650) |
| AP-18 | (SIGMA #A7232) |
| Cinnamaldehyde | (SIGMA #W228613) |
| ATP | (SIGMA #A-6419) |
| 2-Aminoethyl diphenylborinate | (SIGMA #D9754) |
| Menthol | (Sigma #M2772) |
| FLIPR Calcium 3 Assay Kit | (Molecular Devices #R8108) |
| Probenecid | (INVITROGEN #36400) |
| Plates | (BD #35-3962) |

CHO-K1Tet-On HOMSA TRPA1 Clone 20
Chinese Hamster Ovary cells, inducible expression
Clone #20, received at passage #26
Channel expression in this cell line has been shown to be stable for at least 80 passages
Verified Mycoplasma free with MycoAlert Kit
Cell line expanded and banked
Growth Conditions:
Growth Media for CHO-K1 Tet-On_HOMSA_TRPA1_Clone_20
Ham's F-12 with 10% tetracycline-free FBS
1× penicillin-streptomycin
1× glutamax
0.01 mg/ml Blasticidin
0.40 mg/ml Zeocin The cell line doubling rate was ~15 h. The culture plates did not exceed 80% confluency.

To induce expression, tetracycline was added to blasticidin/zeocin-free media at a final concentration of 1 ug/ml. Experiments were run at 24 h post induction.

Plating conditions CHOK1/TRPA1 cells:
Harvested cells with 0.025% trypsin/EDTA.
Resuspended cells in growth media without selection antibiotics.
Measured cell density and diluted to 2.4×10$^5$ cells/ml in media containing 1 ug/ml Doxycycline Plate 25 ul/well into 384 well black/clear tissue culture-treated plates.
Incubated overnight at 37° C.
Calcium Flux Assay:
Day of Assay:
Reagents:
Replacement Buffer: Hank's Balanced Salt Solution, 20 mM HEPES along with 0.005% BSA and 2× Probenecid Dye Loading Buffer: Cal-3 NW Calcium dye was prepared by dissolving the contents of one vial with 500 ml Hank's Balanced Salt Solution containing 20 mM HEPES.
Control compounds for CHOK1/TRPA1 cells:
AP-18, stock 10 mM, prepare 3.5× compound dilution in a Compound Buffer (HBSS/20mM HEPES/0.005% BSA)—final concentration 10 uM.
Preparation of Cinnamaldehyde (agonist addition):
FW=132.16
Specific gravity=1.046 gm/cc
1.32 gm/1.046 gm/cc=1.26 ml of stock
Add 1.74 ml DMSO=3.3 M stock
Working solution 4.5× (final 100 uM in Compound Buffer: HBSS/20 mM HEPES/0.005% BSA)
Compounds dilutions were prepared from 5 or 10 mM stock (100% DMSO):
Adjustments of volumes and concentrations were made at time of titration to reflect desired final assay concentrations.
Compounds were tested at either 20 μM three folds dilution 11 steps out or 30 μM two folds dilution 11 steps out.
3 μl of diluted compound were transferred into Weidmann 384—well plate in duplicates side-by-side.
Compound plates were resuspended with 100 ul of HBSS/20 mM HEPES/0.005% BSA buffer (Compound Buffer):
column 1A-H: buffer/DMSO (bk)
column 2A-H: AP-18(control antagonist for CHOK1 TRPA1 cells)
column 1I-P: ATP (control for CHOK1 teton cells)
column 2 I-P: 2APB (control antagonist for CHOK1/TRPM8 cells).
Growth media was removed from the cell plates (20 ul) and 20 ul of the Replacement Buffer was added followed by addition of 25 ul of diluted dye. All three steps were performed using a Plate Washer BioTek 407. The plates were then incubated for 30' at RT.
After incubation, both the cell and compound plates were brought to the FLIPR and 20 ul of the diluted compounds/antagonist/bk were transferred to the cell plates by the FLIPR. Plates were then incubated for 30' at room temperature. After 30' incubation, plates were returned to the FLIPR and 20 ul of 4.5× Cinnamaldehyde was added to the cell plates. During the compound addition as well as agonist addition, fluorescence readings were taken simultaneously from all 384 wells of the cell plate every 1.5 seconds. Five readings were taken to establish a stable baseline, then 20 μl of sample was rapidly (30 ul/sec) and simultaneously added to each well of the cell plate. The fluorescence was continuously monitored before, during and after sample/agonist addition for a total elapsed time of 100 seconds (compound addition) and 120 seconds (agonist addition). Responses (increase in peak fluorescence) in each well following agonist addition was determined. The initial fluorescence reading from each well, prior to ligand stimulation, was used a zero baseline value for the data from that well. The responses were expressed as % inhibition of the inhibitor control as shown in Table 1 below:

TABLE 1

| Example No. | hTRPA1; IC$_{50}$ uM |
|---|---|
| 1 | 4 |
| 2 | 0.71 |
| 3 | 4.2 |
| 4 | 0.46 |
| 5 | 5.5 |
| 6 | 3.3 |
| 7 | 3.6 |
| 8 | 0.74 |
| 9 | 4.3 |
| 10 | 0.75 |

TABLE 1-continued

| Example No. | hTRPA1; IC$_{50}$ uM |
|---|---|
| 11 | 2.9 |
| 12 | 5.6 |
| 13 | 3.5 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
|---|---|
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:

1. A compound of formula (I)

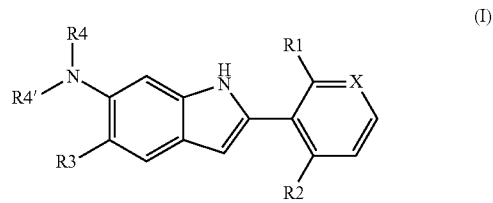

wherein:
X is —CH— or nitrogen;
R1 is lower alkoxy;
R2 is halogen;
R3 is hydrogen or lower alkoxy;
one of R4 or R4' is hydrogen or lower alkyl and the other is hydrogen or —C(O)—R5; and
R5 is alkoxy, —CF$_3$, —CHF$_2$, lower alkyl, chlorophenyl or (fluoro-benzenesulfonyl)-piperidinyl;
or a pharmaceutically acceptable salt thereof.

2. A compound according to claim 1, wherein X is nitrogen.

3. A compound according to claim 1, wherein R1 is methoxy.

4. A compound according to claim 1, wherein R2 is iodine or chlorine.

5. A compound according to claim 1, wherein R3 is hydrogen or methoxy.

6. A compound according to claim 1, wherein R$^3$ is hydrogen.

7. A compound according to claim 1, wherein R4 and R4' are both hydrogen.

8. A compound according to claim 1, wherein R5 is methyl, tert-butoxy, —CF$_3$, —CHF$_2$, chlorophenyl or (fluoro-benzenesulfonyl)-piperidinyl.

9. A compound according to claim 1, wherein R5 is —CF$_3$.

10. A compound according to claim 1 selected from
[2-(4-Iodo-2-methoxy-pyridin-3-yl)-1H-indol-6-yl]-carbamic acid tert-butyl ester;
2,2,2-Trifluoro-N-[2-(4-iodo-2-methoxy-pyridin-3-yl)-1H-indol-6-yl]-acetamide;
2,2-Difluoro-N-[2-(4-iodo-2-methoxy-pyridin-3-yl)-1H-indol-6-yl]-acetamide;
N-[2-(4-Chloro-2-methoxy-pyridin-3-yl)-1H-indol-6-yl]-2,2,2-trifluoro-acetamide;
[2-(4-Iodo-2-methoxy-pyridin-3-yl)-1H-indol-6-yl]-methyl-amine;
2,2-Difluoro-N-[2-(4-iodo-2-methoxy-pyridin-3-yl)-1H-indol-6-yl]-N-methyl-acetamide;
N-[2-(4-Iodo-2-methoxy-pyridin-3-yl)-1H-indol-6-yl]-N-methyl-acetamide;
2-(4-Iodo-2-methoxy-pyridin-3-yl)-5-methoxy-1H-indol-6-ylamine;
2-(2-Chloro-6-methoxy-phenyl)-1H-indol-6-ylamine;
N-[2-(2-Chloro-6-methoxy-phenyl)-1H-indol-6-yl]-2,2,2-trifluoro-acetamide;
3-Chloro-N-[2-(4-iodo-2-methoxy-pyridin-3-yl)-1H-indol-6-yl]-benzamide;
3-Chloro-N-[2-(4-chloro-2-methoxy-pyridin-3-yl)-1H-indol-6-yl]-benzamide; and (S)-1-(4-Fluoro-benzenesulfonyl)-piperidine-2-carboxylic acid[2-(4-chloro-2-methoxy-pyridin-3-yl)-1H-indol-6-yl]-amide.

11. A pharmaceutical composition comprising a therapeutically effective amount of a compound of claim 1 and a pharmaceutically acceptable carrier.

12. A method for the treatment of a respiratory disorder, comprising the step of administering a therapeutically effective amount of a compound according to claim 1 to a subject in need thereof.

13. The method of claim 12, wherein the respiratory disorder is selected from the group consisting of chronic obstructive pulmonary disorder (COPD), asthma, allergic rhinitis, and bronchospasm.

* * * * *